United States Patent
Mault

(10) Patent No.: US 6,612,306 B1
(45) Date of Patent: Sep. 2, 2003

(54) RESPIRATORY NITRIC OXIDE METER

(75) Inventor: James R. Mault, Evergreen, CO (US)

(73) Assignee: Healthetech, Inc., Golden, CO (US)

( * ) Notice: Subject to any disclaimer, the term of this patent is extended or adjusted under 35 U.S.C. 154(b) by 47 days.

(21) Appl. No.: 09/685,439

(22) Filed: Oct. 11, 2000

Related U.S. Application Data

(60) Provisional application No. 60/236,829, filed on Sep. 29, 2000, provisional application No. 60/228,388, filed on Aug. 28, 2000, and provisional application No. 60/159,285, filed on Oct. 13, 1999.

(51) Int. Cl.$^7$ .............................................. A61M 16/00
(52) U.S. Cl. ......................... 128/204.22; 128/200.24; 128/200.22; 128/204.23; 128/205.23
(58) Field of Search ................... 128/200.24, 202.22, 128/204.21, 204.22, 204.23, 205.23; 600/532

(56) References Cited

U.S. PATENT DOCUMENTS

| | | | |
|---|---|---|---|
| 2,630,798 A | 3/1953 | White et al. ............... | 128/2.07 |
| 2,826,912 A | 3/1958 | Kritz ........................... | 73/194 |
| 2,831,348 A | 4/1958 | Kritz ........................ | 73/861.28 |
| 2,838,399 A | 6/1958 | Vogel, Jr. ...................... | 99/48 |
| 2,869,357 A | 11/1959 | Kritz ............................. | 73/32 |
| 2,911,825 A | 11/1959 | Kritz ........................... | 73/194 |
| 2,920,012 A | 1/1960 | Sanders et al. | |
| 3,213,684 A | 10/1965 | Seaton et al. ................. | 73/190 |

(List continued on next page.)

FOREIGN PATENT DOCUMENTS

| | | |
|---|---|---|
| DE | 198 10 476 | 9/1998 |
| EP | 0459647 A2 | 12/1991 |
| EP | 0 712 638 | 12/1995 |
| GB | 2323292 | 9/1998 |
| WO | WO 96/40340 | 12/1996 |

OTHER PUBLICATIONS

Frederick P. Schwarz et al., Fluorescence Detection of Nitric Oxide in Nitrogen, Apr. 1975, Analyticial Chemistry, vol. 47, No. 4, pp. 703–707.*

Medical Progress Through Technology, vol. 9, No. 1, 1982 Berlin (D), pp. 27–32, R. Salminen et al., "Computerized Breath–By–Breath Analysis of Respiratory Variables During Exercise."

British Journal Of Anaesthesia, vol. 49, 1977 London (GB) pp. 575–587, J. A. Bushman et al. "Closed Circuit Anaesthesia."

IEEE Transactions on Biomedical Engineering, vol. 35, No. 9, Sep. 1988, pp. 653–659, Capek et al., "Noninvasive Measurement of Cardia Output Using Partial CO2 ReBreathing."

Clinics in Chest Medicine (Review), vol. 10, 1989, pp. 255–264, Heigenhauser et al., "Meausurement if Cardiac Output by Carbon Dioxide Rebreathing Methods."

Determination Of Nitric Oxide Levels By Fluorescence Spectroscopy, Gabor G. and Allon, N. in Biochemical, Pharmacological, and Clinical Aspects of Nitric Oxide, edited by B. A. Weissman et al, Plenum Press, New York, 1995, pp. 57.

*Primary Examiner*—Aaron J. Lewis
(74) *Attorney, Agent, or Firm*—Gifford, Krass, Groh, Sprinkle, Anderson & Citkowski, P.C.

(57) ABSTRACT

A respiratory nitric oxide meter includes a respiratory connector designed to be supported in contact with a subject and to pass respiratory gases as the subject breathes. A flow pathway receives and passes the respiration gases. One end of the pathway is in fluid communication with the respiratory connector, and the other end is in fluid communication with a reservoir of respiratory gases. A nitric oxide concentration sensor generates electrical signals as a function of the instantaneous fraction of nitric oxide as the respiration gases pass through the flow pathway.

8 Claims, 6 Drawing Sheets

U.S. PATENT DOCUMENTS

| | | |
|---|---|---|
| 3,220,255 A | 11/1965 | Scranton et al. ............... 73/204 |
| 3,250,270 A | 5/1966 | Bloom ....................... 128/2.07 |
| 3,306,283 A | 2/1967 | Arp ............................ 128/2.07 |
| 3,523,529 A | 8/1970 | Kissen ....................... 128/2.07 |
| 3,527,205 A | 9/1970 | Jones ......................... 128/2.08 |
| 3,681,197 A | 8/1972 | Smith ........................... 195/63 |
| 3,726,270 A | 4/1973 | Griffis et al. ............... 128/2.08 |
| 3,799,149 A | 3/1974 | Rummel et al. ............ 128/2.07 |
| 3,814,091 A | 6/1974 | Henkin ........................ 128/188 |
| 3,834,375 A | 9/1974 | Sanctuary et al. .......... 128/2.07 |
| 3,895,630 A | 7/1975 | Bachman .................... 128/2.07 |
| 3,938,551 A | 2/1976 | Henkin ........................ 137/613 |
| 3,962,917 A | 6/1976 | Terada .......................... 73/204 |
| 3,979,480 A | 9/1976 | Radici et al. ............... 128/2.08 |
| 4,003,396 A | 1/1977 | Fleischmann ................. 137/83 |
| 4,051,847 A | 10/1977 | Henkin .................... 128/145.6 |
| 4,078,554 A | 3/1978 | Lemaitre et al. ........... 128/2.08 |
| 4,111,036 A | 9/1978 | Frechette et al. ............... 73/23 |
| 4,186,735 A | 2/1980 | Henneman et al. .... 128/201.25 |
| 4,188,946 A | 2/1980 | Watson et al. ......... 128/204.22 |
| 4,197,857 A | 4/1980 | Osborn ........................ 600/531 |
| 4,200,094 A | 4/1980 | Gedeon et al. ........ 128/201.13 |
| 4,211,239 A | 7/1980 | Raemer et al. ............. 128/716 |
| 4,221,224 A | 9/1980 | Clark .......................... 128/718 |
| 4,230,108 A | 10/1980 | Young |
| 4,341,867 A | 7/1982 | Johansen ..................... 435/189 |
| 4,359,057 A | 11/1982 | Manzella .................... 128/718 |
| 4,368,740 A | 1/1983 | Binder ........................ 128/717 |
| 4,386,604 A | 6/1983 | Hershey ...................... 128/718 |
| 4,425,805 A | 1/1984 | Ogura et al. ............. 73/861.29 |
| 4,440,177 A | 4/1984 | Anderson et al. ........... 600/532 |
| 4,444,201 A | 4/1984 | Itoh ............................ 128/716 |
| 4,463,764 A | 8/1984 | Anderson et al. ........... 600/532 |
| 4,572,208 A | 2/1986 | Cutler et al. ................ 128/718 |
| 4,598,700 A | 7/1986 | Tamm ........................ 128/671 |
| 4,608,995 A | 9/1986 | Linnarsson et al. ......... 128/713 |
| 4,619,269 A | 10/1986 | Cutler et al. ................ 128/719 |
| 4,637,987 A | 1/1987 | Minten et al. .............. 436/151 |
| 4,648,396 A | 3/1987 | Raemer ....................... 600/534 |
| 4,658,832 A | 4/1987 | Brugnoli ..................... 600/532 |
| 4,753,245 A | 6/1988 | Gedeon ....................... 128/718 |
| 4,756,670 A | 7/1988 | Arai ............................. 417/43 |
| 4,781,184 A | 11/1988 | Fife ........................ 128/205.12 |
| 4,796,639 A | 1/1989 | Snow et al. ................. 600/532 |
| 4,850,371 A | 7/1989 | Broadhurst et al. ......... 600/532 |
| 4,856,531 A | 8/1989 | Merilainen .................. 600/532 |
| 4,909,259 A | 3/1990 | Tehrani ....................... 600/531 |
| 4,914,959 A | 4/1990 | Mylvaganam et al. ... 73/861.28 |
| 4,917,108 A | 4/1990 | Mault ......................... 128/718 |
| 4,955,946 A | 9/1990 | Mount et al. ................ 600/532 |
| 4,986,268 A | 1/1991 | Tehrani ....................... 128/204 |
| 4,998,018 A | 3/1991 | Kurahashi et al. .......... 250/343 |
| 5,022,406 A | 6/1991 | Tomlinson .................. 128/719 |
| 5,038,773 A | 8/1991 | Norlien et al. ......... 128/205.23 |
| 5,038,792 A | 8/1991 | Mault ......................... 128/718 |
| 5,042,500 A | 8/1991 | Norlien et al. .............. 600/532 |
| 5,042,501 A | 8/1991 | Kenny et al. ................ 600/532 |
| 5,060,506 A | 10/1991 | Douglas ....................... 73/24.1 |
| 5,060,655 A | 10/1991 | Rudolph ..................... 128/716 |
| 5,060,656 A | 10/1991 | Howard ...................... 128/718 |
| 5,069,220 A | 12/1991 | Casparie et al. ............. 128/719 |
| 5,072,737 A | 12/1991 | Goulding .................... 128/718 |
| 5,081,871 A | 1/1992 | Glaser ...................... 73/863.23 |
| 5,095,900 A | 3/1992 | Fertig et al. ............. 128/207.14 |
| 5,095,913 A | 3/1992 | Yelderman et al. .......... 128/719 |
| 5,117,674 A | 6/1992 | Howard ..................... 73/31.07 |
| 5,119,825 A | 6/1992 | Huhn ......................... 600/529 |
| 5,178,155 A | 1/1993 | Mault ........................ 128/718 |
| 5,179,958 A | 1/1993 | Mault ........................ 128/718 |
| 5,214,966 A | 6/1993 | Delsing ................... 73/861.28 |
| 5,233,996 A | 8/1993 | Coleman et al. ........... 600/529 |
| 5,282,473 A | 2/1994 | Braig et al. ................. 600/532 |
| 5,285,794 A | 2/1994 | Lynch ........................ 128/719 |
| 5,293,875 A | 3/1994 | Stone ......................... 128/719 |
| 5,299,579 A | 4/1994 | Gedeon et al. ............. 600/532 |
| 5,303,712 A | 4/1994 | Van Duren ................. 600/529 |
| 5,309,921 A | 5/1994 | Kisner et al. ............... 600/532 |
| 5,326,973 A | 7/1994 | Eckerbom et al. .......... 250/343 |
| 5,355,879 A | 10/1994 | Brain |
| 5,357,972 A | 10/1994 | Norlien ...................... 128/725 |
| 5,363,857 A | 11/1994 | Howard ...................... 600/531 |
| 5,398,695 A | 3/1995 | Anderson et al. ........... 600/532 |
| 5,402,796 A | 4/1995 | Packer et al. ............... 128/719 |
| 5,419,326 A | 5/1995 | Harnoncourt .......... 128/660.02 |
| 5,425,374 A | 6/1995 | Ueda et al. ................. 600/532 |
| 5,447,165 A | 9/1995 | Gustafsson ................. 128/719 |
| 5,450,193 A | 9/1995 | Carlsen et al. .............. 356/301 |
| 5,468,961 A | 11/1995 | Gradon et al. .............. 250/345 |
| 5,503,151 A | 4/1996 | Harnoncourt et al. .. 128/660.02 |
| 5,517,313 A | 5/1996 | Colvin, Jr. ................... 356/417 |
| 5,540,233 A | 7/1996 | Larsson et al. ............. 128/725 |
| 5,558,083 A * | 9/1996 | Bathe et al. ........... 128/203.12 |
| 5,570,697 A | 11/1996 | Walker et al. .............. 128/719 |
| 5,616,826 A | 4/1997 | Pellaux et al. ............. 73/24.02 |
| 5,632,281 A | 5/1997 | Rayburn ..................... 128/719 |
| 5,645,071 A | 7/1997 | Harnoncourt et al. ....... 128/719 |
| 5,647,370 A | 7/1997 | Harnoncourt ............... 128/725 |
| 5,676,132 A | 10/1997 | Tillotson et al. ........ 128/204.23 |
| 5,705,735 A | 1/1998 | Acorn ......................... 73/23.3 |
| 5,754,288 A | 5/1998 | Yamamoto et al. .......... 356/301 |
| 5,789,660 A | 8/1998 | Kofoed et al. ................. 73/232 |
| 5,795,787 A | 8/1998 | Silkoff et al. ................ 436/116 |
| 5,796,009 A | 8/1998 | Delsing ................... 73/861.28 |
| 5,800,360 A | 9/1998 | Kisner et al. ............... 600/532 |
| 5,816,246 A | 10/1998 | Mirza ......................... 128/726 |
| 5,831,175 A | 11/1998 | Fletcher-Haynes ....... 73/861.28 |
| 5,834,626 A | 11/1998 | DeCastro et al. ............ 73/23.3 |
| 5,836,300 A | 11/1998 | Mault .................... 128/204.23 |
| 5,839,433 A | 11/1998 | Higenbottam .......... 128/204.21 |
| 5,873,359 A | 2/1999 | Zapol et al. ............ 128/203.12 |
| 5,894,351 A | 4/1999 | Colvin, Jr. ................... 356/417 |
| 5,904,938 A | 5/1999 | Zapol et al. ................. 424/718 |
| 5,910,661 A | 6/1999 | Colvin, Jr. ................... 250/573 |
| 5,917,605 A | 6/1999 | Colvin, Jr. ................... 356/417 |
| 5,922,610 A | 7/1999 | Alving et al. ............... 436/116 |
| 5,932,812 A | 8/1999 | Delsing ................... 73/861.02 |
| 5,957,128 A | 9/1999 | Hecker et al. .......... 128/204.22 |
| 5,957,858 A | 9/1999 | Micheels et al. ............ 600/532 |
| 6,010,459 A | 1/2000 | Silkoff et al. ................ 600/532 |
| 6,033,368 A | 3/2000 | Gaston, IV et al. ......... 600/532 |
| 6,038,913 A | 3/2000 | Gustafsson et al. .......... 73/23.3 |
| 6,044,843 A | 4/2000 | O'Neil et al. ........... 128/204.23 |
| 6,062,064 A | 5/2000 | Yoshida et al. .............. 73/23.2 |
| 6,063,027 A | 5/2000 | Alving et al. ............... 600/300 |
| 6,063,407 A | 5/2000 | Zapol et al. ................. 424/718 |
| 6,067,983 A | 5/2000 | Stenzler .................. 128/204.23 |
| 6,082,176 A | 7/2000 | Kondo et al. ............... 73/23.31 |
| 6,082,177 A | 7/2000 | Niazy et al. ................ 73/23.31 |
| 6,117,872 A | 9/2000 | Maxwell et al. ............. 514/249 |
| 6,345,538 B1 * | 2/2002 | Krahbichler et al. ...... 73/861.27 |

* cited by examiner

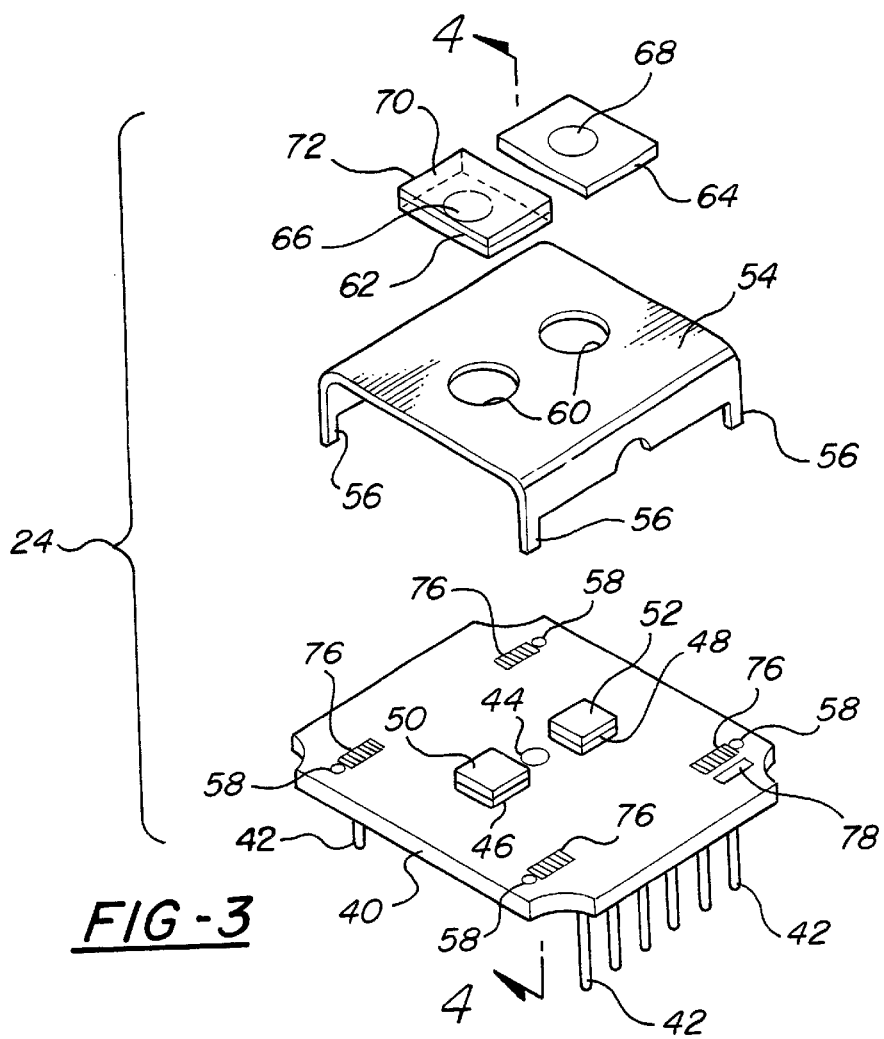

RESPIRATORY NITRIC OXIDE METER

REFERENCE TO RELATED APPLICATION

This application claims priority from U.S. provisional patent application Ser. Nos. 60/159,285, filed Oct. 13, 1999; 60/228,388, filed Aug. 28, 2000; and 60/236,829, filed Sep. 29, 2000, the entire contents of all of which are incorporated herein by reference.

FIELD OF THE INVENTION

The present invention relates generally to the detection of nitric oxide in a gaseous mixture and, more specifically, to the detection of nitric oxide in a flow pathway.

BACKGROUND OF THE INVENTION

Definition of Nitric Oxide

Nitric oxide, NO, is a colorless gas useful in the detection and treatment of a variety of medical conditions such as asthma. Nitric oxide, NO, should not be confused with nitrous oxide, $N_2O$, or nitrogen dioxide, $NO_2$. Nitrogen and oxygen also form other compounds, especially during combustion processes. These typically take the form of $NO_x$ where x represents an integer. These forms are generally referred to as NOX. Detection of nitric oxide, NO, is the primary focus of the present application. Nitric oxide has a variety of beneficial uses and detection of nitric oxide, especially in small concentrations, is necessary for the proper administration of nitric oxide and diagnosis of disease.

Use of Nitric Oxide in Treatment of Physiological Conditions

Nitric oxide is beneficial in both the treatment and diagnosis of asthma and other forms of lung disorders. Asthma is a chronic disease characterized by intermittent, reversible, widespread constriction of the airways of the lungs in response to any of a variety of stimuli that do not affect the normal lung. A variety of drugs are commonly used to treat asthma. It is known that inhalation of nitric oxide (NO) is therapeutically beneficial in the prevention and treatment of asthma attacks and other forms of bronchoconstriction, of acute respiratory failure, or of reversible pulmonary vasoconstriction as discussed in U.S. Pat. No. 5,873,359 to Zapol et al, incorporated herein by reference. U.S. Pat. Nos. 5,904,938 and 6,063,407, both to Zapol et al. and incorporated herein by reference, disclose the use of inhaled nitric oxide in the treatment of vascular thrombosis and retinosis. Typically, treatment utilizing nitric oxide includes the introduction of nitric oxide as a portion of the respiratory gases being inhaled by the patient. The nitric oxide concentration is usually in the range of 1 to 180 parts per million (ppm). The difficulty presented in the administration of controlled amounts of nitric oxide is the determination of the concentration being introduced. It has traditionally been very difficult to quickly and accurately determine the concentration of nitric oxide in the gas mixture, especially where the concentration of nitric oxide is very low.

U.S. Pat. No. 5,839,433 to Higenbottam, incorporated herein by reference, describes the use of nitric oxide in the treatment of certain lung diseases and conditions. As discussed in the specification, a drawback to the administration of gaseous nitric oxide is that it rapidly converts to nitrogen dioxide, a potentially harmful substance. Consequently, it is often preferable to intubate the patient so that nitric oxide is administered directly to the lungs. Whether or not intubated, it is very important to accurately monitor the amount of nitric oxide being introduced to the lungs. The Higenbottam reference proposes an improvement wherein the nitric oxide is introduced as a short pulse of known volume, rather than continuously during inhalation.

U.S. Pat. No. 5,531,218 to Krebs, incorporated herein by reference, discusses the benefits of nitric oxide inhalation in the treatment of various disorders, including adult respiratory distress syndrome, (ARDS). The specification discloses a system for administering nitric oxide that includes a source of nitric oxide, an analyzer for analyzing nitric oxide concentration, and a control unit, with the analyzer and the control unit cooperating to maintain the appropriate nitric oxide concentration. However, this system relies on the use of nitric oxide sensors utilizing infrared absorption measurement, electrochemical sensors, or chemiluminescence detectors. Each of these analyzers have drawbacks and cannot provide instantaneous nitric oxide concentration measurements.

Use of Nitric Oxide in Diagnosis

Nitric oxide may also be used in the diagnosis of various physiological conditions. For example, the reversibility of chronic pulmonary vasorestriction may be diagnosed by administering known quantities of nitric oxide and monitoring changes in pulmonary arterial pressure (PAP) and cardiac output as described in U.S. Pat. No. 5,873,359 to Zapol et al.

Endogenous production of nitric oxide in the human airway has been shown to be increased in patients with asthma and other inflammatory lung diseases. Expired nitric oxide concentrations are also elevated in patients with reactive airways disease. Therefore, detection of nitric oxide is beneficial in diagnosing these conditions. However, proper diagnosis requires accurate measurement of nitric oxide in parts per billion (ppb) of gas-phase nitric oxide.

Determination of the level of nitric oxide is useful in the diagnosis of inflammatory conditions of the airways, such as allergic asthma and rhinitis, in respiratory tract infections in humans and Kartagener's syndrome. It also has been noted that the level of nitric oxide in the exhalation of smokers is decreased. U.S. Pat. No. 5,922,610 to Alving et al., incorporated herein by reference, discusses the detection of nitric oxide in diagnosing these conditions, as well as gastric disturbances.

In addition to the above, nitric oxide may be used in the determination of lung function. For example, U.S. Pat. No. 5,447,165 to Gustafsson, incorporated herein by reference, explains that nitric oxide in exhalation air is indicative of lung condition. As one test of lung function, a subject may inhale a trace gas, such as nitric oxide. Then the concentration and time-dispersment of the gas in the exhalation air is measured. The shape of the curve representing the time dependent gas concentration in the exhalation air is indicative of lung function or condition. Obviously, it is necessary to have an accurate determination of both the concentration and the time-dependence of the concentration to allow for the most accurate diagnosis.

During exhalation, gas mixture changes during the breath. The initial portion of the exhalation is "dead space" air that has not entered the lungs. This includes the respiratory gases in the mouth and respiratory passages above the lungs. Also, some portion of the exhalation measured by an analytical instrument may be attributed to dead air in the mask and flow passages of the apparatus. As a breath continues, respiratory gases from within the lungs are exhaled. The last portion of respiratory gases exhaled is considered alveolar air. Often it is beneficial to measure gas concentrations in alveolar air to determine various pulmonary parameters. For example, nitric oxide, as an indicator of various disease states, may be concentrated in the alveolar air. However, nitric oxide is also produced by various mucus membranes and therefore nitric oxide may be present in both the dead air space and in the alveolar air. During an exhalation, the dead air space may be overly contaminated with nitric oxide due to residence in the mouth and nasal cavities where nitric oxide is absorbed from the mucus membranes. Therefore, it is necessary to distinguish the various portions of exhalation for proper diagnosis. U.S. Pat. No. 6,038,913 to Gustafsson et al., incorporated herein by reference, discusses having an exhalation occur with very little resistance during an initial "dead space" phase of exhalation and then creating resistance against the remaining portion of the exhalation.

Nitric Oxide Measurement Methods

Numerous approaches have been used and proposed for monitoring the concentration of nitric oxide in a gas mixture. These include mass spectroscopy, electrochemical analysis, calorimetric analysis, chemiluminescence analysis, and piezoelectric resonance techniques. Each of these approaches have shortcomings that make them poorly suited to widespread use in the diagnosis and treatment of disease.

Mass spectroscopy utilizes a mass spectrometer to identify particles present in a substance. The particles are ionized and beamed through an electromagnetic field. The manner in which the particles are deflected is indicative of their mass, and thus their identity. Mass spectroscopy is accurate but requires the use of very expensive and complicated equipment. Also, the analysis is relatively slow, making it unsuitable for real time analysis of exhalations. Preferably, in the breath by breath analysis of nitric oxide, it is desirable to quickly and accurately measure the nitric oxide concentration in the flow path as the gas mixture flows through the flow path. Mass spectroscopy requires sampling of portions of the gas mixture rather than analyzing the nitric oxide concentration in the flow pathway itself. Mass spectroscopy cannot be considered an instantaneous or continuous analysis approach. It requires dividing the exhalation into multiple discrete samples and individual analysis of each sample. This does not create a curve of the nitric oxide concentration but instead creates a few discreet points. Sampling-based systems are especially deficient when detecting gases in very low concentrations since large samples are required.

Electrochemical-based analysis systems use an electrochemical gaseous sensor in which gas from a sample diffuses into and through a semi-permeable barrier, such as membrane, then through an electrolyte solution, and then to one of typically three electrodes. At one of the three electrodes, a sensing redox reaction occurs. At the second, counter, electrode, a complimentary and opposite redox reaction occurs. A third electrode is typically provided as a reference electrode. Upon oxidation, or reduction, of the nitric oxide at the sensing electrode, a current flows between the sensing and counter electrode that is proportional to the amount of nitric oxide reacting at the sensing electrode surface. The reference electrode is used to maintain the sensing electrode at a fixed voltage. A typical electrochemical-based gas analyzer for detecting nitric oxide is shown is U.S. Pat. No. 5,565,075 to Davis et al, incorporated herein by reference. Electrochemical-based devices have high sensitivity and accuracy, but typically have a response time in excess of 30 seconds. This is significantly too slow to allow breath by breath, or continuous, analysis of respiration gases.

Colorimetric analysis relies on a chemical reaction by a gas which provides a corresponding change in pH, thereby triggering a color change in an indicator. This approach requires expendable chemical substances. Also, this approach is often disturbed by the presence of other gases, particularly the relative amount of humidity present. Response times are too slow for analysis during a breath.

Chemiluminescent-based devices depend on the oxidation of nitric oxide by mixing the nitric oxide with ozone, $O_3$, to create nitrogen dioxide and oxygen. The nitrogen dioxide is in an excited state immediately following the reaction and releases photons as it decays back to a non-excited state. By sensing the amount of light emitted during this reaction, the concentration of nitric oxide maybe determined. An example of a chemiluminescent-based device is shown in U.S. Pat. No. 6,099,480 to Gustafsson, incorporated herein by reference. Chemiluminescent devices have response times as fast as about two hundred milliseconds, have high sensitivity, repeatability, and accuracy. However, like with mass spectroscopy, and electrochemical analysis, chemiluminescent analysis requires sampling of the gas mixture rather than continuous analysis of the gas concentration in the flow path itself. Also, chemiluminescent devices are typically very large and expensive.

Piezoelectric resonance techniques are sometimes referred to as MEMS (microelectro-mechanical systems) sensor devices. Basically, a micro-etched cantilevered beam is coated with a "capture" molecule that is specific to the gas being analyzed. In theory, the capture molecule will capture the gas being analyzed in proportion to its ambient concentration. This alters the mass of the micro-etched cantilevered beam. Changes in mass of the beam may theoretically be detected based on changes in its resonant frequency. The change in resonant frequency should be directly proportional to the concentration of the gas being studied. A system for detecting air pollutants is disclosed in U.S. Pat. No. 4,111,036 to Frechette et al., incorporated herein by reference. While the theory behind piezoelectric resonance techniques is rather simple, there has been no known success to date in the analysis of nitric oxide concentrations.

U.S. Pat. No. 6,033,368 to Gaston IV et al. discloses an analyzer for measuring exhaled nitrogen oxides, nitrite and nitrate in very low concentrations. The analyzer includes a chilled exhalation passage which causes lung fluid vapors to collect. The resulting liquid is then analyzed using standard calorimetric assays. While somewhat simpler than other methods, the Gaston apparatus remains complicated, requiring prefreezing of the chilling apparatus, and subsequent analysis of the collected liquid.

Each of the above-described approaches for the use and detection of nitric oxide would benefit from a nitric oxide meter capable of continuously determining the nitric oxide concentration of a flow of respiratory gases in a flow pathway without the need for sampling the mixture. Most preferably, such a meter would provide nearly instantaneous response times so that analysis may be made during a breath or on a breath-by-breath basis.

SUMMARY OF THE INVENTION

The present invention overcomes many of the shortcomings of the prior art by providing a nitric oxide meter designed to provide continuous, or breath-by-breath, analysis. The nitric oxide meter includes a respiratory connector designed to be supported in contact with a subject so as to pass respiratory gases when the subject breathes. A flow pathway receives and passes respiration gases. One end of the flow pathway has in fluid communication with the respiratory connector, and the other end is in fluid communication with a source and sink of respiratory gases. A nitric oxide concentration sensor generates electrical signals as a function of the instantaneous fraction of nitric oxide in the respiration gases as the gases pass through the flow pathway. In some embodiments of the present invention, a flow meter is also provided in the respiratory nitric oxide meter. The flow meter may be an ultrasonic flow meter including a pair of spaced-apart ultrasonic transducers. In other embodiments of the present invention, the respiratory nitric oxide meter forms part of a system for the controlled administration of nitric oxide to the subject. This system includes a nitric oxide regulator designed to selectively introduce nitric oxide into inhalation gases in the pathway. The system may also include a controller which controls the regulator based on signals received from the nitric oxide concentration sensor so as to maintain the instantaneous fraction of nitric oxide in the inhalation gases within prescribed limits.

According to one aspect of the present invention, there is provided a respiratory nitric oxide meter for measuring the nitric oxide content of respiration gases for a subject, said meter comprising: a respiratory connector configured to be disposed in fluid communication with the respiratory system of the subject so as to pass inhalation and exhalation respiratory gases as the subject breathes; a flow pathway operable to receive and pass the respiration gases, the flow pathway having a first end in fluid communication with the respiratory connector and a second end in fluid communication with a reservoir of respiratory gases; a nitric oxide concentration sensor operable to generate electrical signals as a function of the instantaneous fraction of nitric oxide in the respiration gases as the gases pass through the flow pathway; and a one-way valve located between the respiratory connector and the first end of the flow pathway. The one-way valve is presettable in a first position effective to pass inhalation gases directly into the respiratory connector bypassing the flow pathway, and to pass exhalation gases through the flow pathway so as to contact the nitric oxide concentration sensor, to thereby sense the nitric oxide concentration in the exhalation gases. The one-way valve is also presettable in a second position effective to pass exhalation gases directly from the respiratory connector bypassing the flow pathway, and to pass inhalation gases through the flow pathway so as to contact the nitric oxide concentration sensor, to thereby sense the nitric oxide concentration in the inhalation gases.

The reservoir of respiratory gases may be the atmosphere, or another separate source of respiratory gases.

According to another aspect of the present invention, there is provided a respiratory nitric oxide meter for measuring the nitric oxide content of respiration gases for a subject, the meter comprising: a respiratory connector configured to be disposed in fluid communication with the respiratory system of the subject so as to pass exhalation respiration gases as the subject breathes; a flow pathway operable to receive and pass the exhalation respiration gases, the pathway having a first end in fluid communication with the respiratory connector and a second end in fluid communication with a reservoir of respiratory gases; a flow meter configured to generate electrical signals as a function of the instantaneous flow of respiration gases passing through the flow pathway; and a nitric oxide concentration sensor operable to generate electrical signals as a function of the instantaneous fraction of nitric oxide in the exhalation respiration gases as the gases pass through the flow pathway; the nitric oxide concentration sensor having a response time of less than 200 ms to enable instantaneous analysis of the exhalation respiratory gases during a single breath.

Further features of the invention will be apparent from the description below.

BRIEF DESCRIPTION OF THE DRAWINGS

FIG. 3 is an exploded perspective view of an embodiment of a nitric oxide sensor for use with a nitric oxide meter;

FIG. 4 is a cross-sectional side view of the sensor of FIG. 3 taken along lines 4—4;

DETAILED DESCRIPTION OF THE PREFERRED EMBODIMENTS

The present invention provides a respiratory nitric oxide meter that allows the measurement of the instantaneous nitric oxide concentration in a gaseous mixture as the mixture flows through a flow pathway. Unlike the prior art, the present invention is not a sampling based analyzer, but instead measures the concentration of nitric oxide in the flow pathway itself and has a sufficiently fast response time so as to allow analysis on a breath-by-breath basis and to allow the monitoring of the changes in nitric oxide concentration during a single breath. For the purposes of the present invention, the nitric oxide sensors used as part of the nitric oxide meter are considered instantaneous, with instantaneous being defined as fast enough to allow monitoring of changes in the nitric oxide concentration during a single breath. Investigation has indicated that response times of approximately 200 milliseconds (ms) or less are preferred in order to track changes in nitric oxide concentration, with 100 ms or less being even more preferred. Many of the prior art sensors and analyzers have response times on the order of several seconds, making them unsuitable for breath-by-breath analysis of the nitric oxide concentration of either inhalation of exhalation gases. Also, many are sampling based analyzers and therefore analyze discrete samples. The present invention also allows close correlation between nitric oxide measurements and flow measurements, something not easily accomplished with prior art systems.

Figure 1:
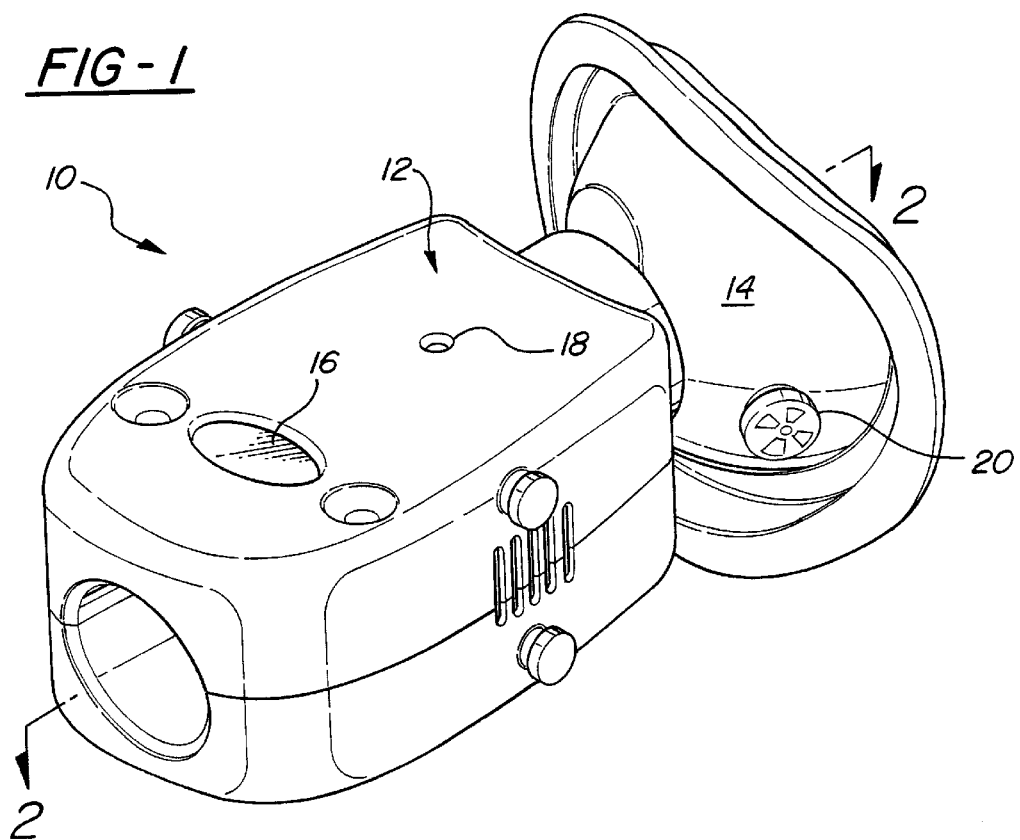
FIG. 1 is a perspective view of the first embodiment of a respiratory nitric oxide meter according to the present invention.
Figure 2:
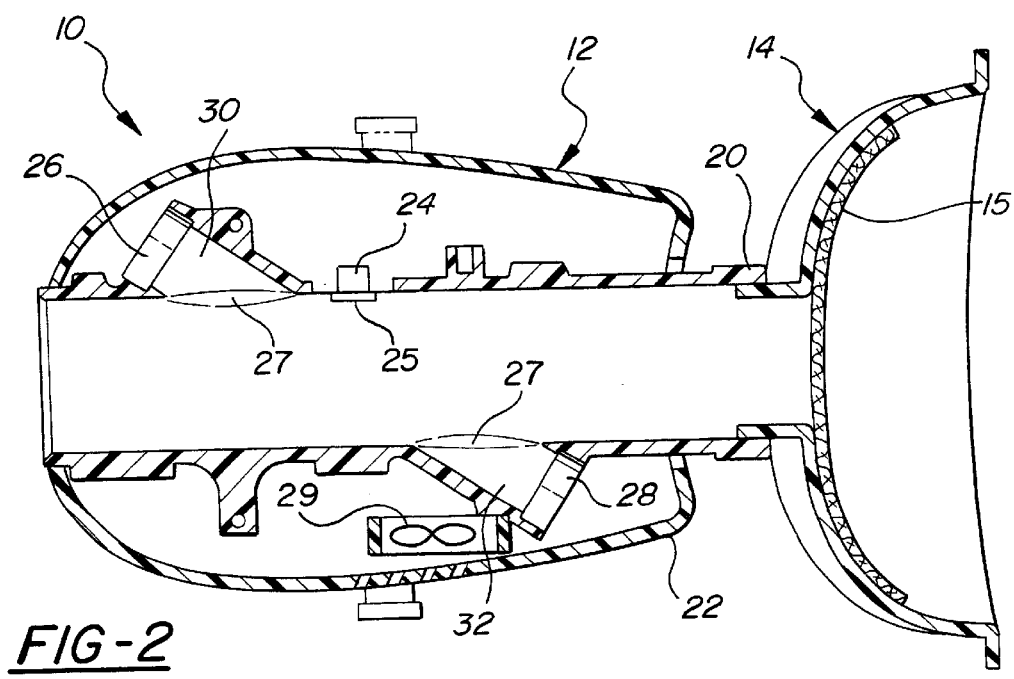
FIG. 2 is a cross-sectional view of the meter of FIG. 1 taken along lines 2—2.

Referring to FIGS. 1 and 2, a first embodiment of a respiratory nitric oxide meter is generally shown at 10. The meter 10 includes a body 12 and a respiratory connector, such as a mask 14, extending from the body 12. Preferably, the meter 10 is a lightweight, handheld or wearable unit. In use, the user grasps the body 12 and brings the mask 14 into contact with their face so that respiratory gases pass through the meter 10. Though not shown, straps may be provided for interconnecting the meter 10 with the user's face and head without the need to support it with a hand.

With the mask 14 in contact with the user's face, the user's inhalations and/or exhalations pass through the body 12 for analysis of the nitric oxide concentration. The meter 10 preferably includes a display 16 as well as a control button 18 for controlling operation of the meter 10.

Depending on the application, the meter 10 may be used to pass inhalation gases, exhalation gases, or both. In situations where it is preferred to pass only inhalation or exhalation gases, but not both, a valve 19 may be provided on the mask for allowing passage of the gases not to be analyzed. For example, the valve 19 may be one-way valve that allows the passage of fresh air into the mask 14 upon inhalation but blocks exhalation, such that exhalation gases pass through the body 12 of the meter 10. By reversing the valve 19, exhalations may be passed through the valve while inhalations enter through the body 12. A second one-way valve may be provided in the body 12 for further directing gases. It will thus be seen that when one-way valve 19 is preset in the first-mentioned position, it is effective to pass inhalation gases directly into the mask respiratory connector 14, bypassing body 12, and to pass exhalation gases through body 12; whereas when the valve 19 is in the second-mentioned position, it is effective to pass exhalation gases from mask 14 bypassing body 12, and to pass inhalation gases through body 12. As described more particularly below, body 12 includes a flow tube containing a nitric oxide concentration sensor, such that when the one-way valve is preset in its first position, the meter senses the nitric oxygen concentration in the exhalation gases, whereas when the valve is in its second position, the meter senses the nitric oxide concentration in the inhalation gases. Without the valve 19, or with the valve disabled, both inhalation and exhalation gases pass through the body 12, such that the nitric oxygen concentration in both the exhalation gases and inhalation gases is sensed.

Referring now to FIG. 2, the meter 10 is shown in cross-section so as to illustrate the internal construction. A flow pathway is formed through the body 12 by a generally straight flow tube 20. At one end, the flow tube 20 is interconnected with the mask 14, and its other end is open to the surrounding air or interconnected with another reservoir of respiratory gases, such as another source and/or sink of respiratory gases. The term "reservoir" as used herein thus also includes the surrounding air. The body 12 includes an outer shell 22 which surrounds the majority of the flow tube 20 so as to provide an improved cosmetic appearance and to support a variety of additional components. As shown, the flow tube 20 is a generally cylindrical tube with a generally constant cross-section throughout its length. Consequently, inhalation and exhalation gases flow very freely into and out of the mask 14, thereby creating little resistance to natural respiration. A nitric oxide sensor 24 is disposed in the side of the flow tube 20 so as to be in contact with respiratory gases passing through the flow tube. The sensor 24 has a sensing face 25 positioned in a window or opening in the side of the tube.

In some embodiments of the present invention, a flow meter is also provided so as to measure the flow of respiratory gases through the flow tube 20. Many types of flow meters may be used. However, in the preferred embodiment, an ultrasonic-based flow meter is used. Ultrasonic flow meters measure the instantaneous flow velocity of gas in a flow tube, thereby allowing determination of flow volumes. In the embodiment shown in FIG. 2, a pair of spaced-apart ultrasonic transducers 26 and 28 are disposed in the ends of a pair of side passages 30 and 32 which branch off of the flow tube 20. Ultrasonically transparent covers 27 may be provided where the side passages 26 and 28 intersect the flow tube 20 to reduce or prevent flow disturbances at the intersections. The ultrasonic transducers 26 and 28 and the side branches 30 and 32 are arranged such that ultrasonic pulses traveling between the transducers 26 and 28 pass through the flow tube 20 at an angle to its central axis. That is, ultrasonic pulses traveling between the transducers 26 and 28 travel along a path which is angled to the path of flow of respiratory gases through the flow tube 20. As shown, the side passages 30 and 32 essentially form an interrupted tube which intersects the flow tube 20 at an angle. As will be clear to those of skill in the art, ultrasonic pulses traveling between the transducers 26 and 28 have a component of their direction of travel which is parallel to the direction of flow of respiratory gases through the flow tube 20.

Measurement of flow velocity using ultrasonic pulses is described in U.S. Pat. Nos. 5,419,326; 5,503,151; 5,645,071; and 5,647,370, all to Harnoncourt et al, which are incorporated herein by reference. In the Harnoncourt patents, ultrasonic transducers are positioned so as to transmit pulses through a flowing fluid in a direction that has a component in the flow direction. Specifically, with fluid flowing through a tube, the transducers are positioned in the side walls of the tube at an angle such that ultrasonic pulses are transmitted at an angle to the fluid flow. Flow speed may be calculated based on the fact that ultrasonic pulses traveling with the flow travel faster while ultrasonic pulses traveling against the flow travel slower. Mathematical corrections are made for the fact that the ultrasonic pulses are traveling at an angle to the flow. Preferably, pulses are alternately transmitted in a direction with the flow and in a direction against the flow so that a time difference may be calculated. The present invention may use ultrasonic transducers comprising a metalized polymer film and a perforated metal sheet. In one preferred embodiment, the ultrasonic flow measurement system is supplied by NDD of Zurich, Switzerland and Chelmsford, Mass.

Ultrasonic pulses are transmitted with and against the direction of flow, resulting in measurement of upstream and downstream transit times. If the gas flow rate is zero, the transit times in either direction through the gas are the same, being related to the speed of sound and distance traveled. However, with gas flow present, the upstream transit times differ from the downstream transit times. For constant flow, the difference between sequential upstream and downstream transit times is directly related to the gas flow speed. Further details of this approach to ultrasonic flow sensing may be obtained by reference to Applicant's co-pending patent application Ser. No. 09/630,398, which is incorporated herein in its entirety by reference. Processing circuitry and additional sensors may be provided within the housing 12 for processing signals from the ultrasonic sensors 26 and 28, as also described in Applicant's co-pending application referred to above. Also, a fan 29 may be provided to force fresh air over some of the internal circuitry. As shown, the nitric oxide sensor 24 is positioned in the wall of the flow tube 20 approximately midway between the ultrasonic transducers 26 and 28. Therefore, the same portion of the flow is measured for flow speed and nitric oxide concentration at the same time, allowing coordination of the data.

Referring now to FIGS. 3 and 4, one embodiment of a nitric oxide sensor 24 is shown. Preferably, instantaneous nitric oxide concentration is measured at the same time flow is measured. In the presently preferred embodiment of the present invention, a fluorescence-based nitric oxide sensor is used to determine the partial pressure of nitric oxide in the respiration gases passing through the flow tube 20.

Fluorescence based oxygen sensors are known in the art, for example as described by Colvin (U.S. Pat. Nos. 5,517, 313; 5,894,351; 5,910,661; and 5,917,605; and PCT International Publication WO 00/13003, all of which are incorporated herein by reference). A sensor typically comprises an oxygen permeable film in which oxygenindicating fluorescent molecules are embedded. In U.S. Pat. Nos. 5,517, 313 and 5,894,351, Colvin describes sensors using a silicone polymer film, and suggests using a ruthenium complex, tris(4,7-diphenyl-1,10-phenanthroline)ruthenium (II) perchlorate, as the oxygen indicator fluorophore molecule. The orange-red fluorescence of this ruthenium complex is quenched by the local presence of oxygen. Oxygen diffuses into the oxygen permeable film from the gas flowing over the film, inducing fluorescence quenching. The time response of the quenching effect, relative to concentration changes of oxygen in the gas outside the film, is related to the thickness of the film. Thin films are preferred for a rapid response, as described in U.S. Pat. No. 5,517,313.

Referring now to FIGS. 3 and 4, the fluorescence based nitric oxide sensor used in the present embodiment is shown generally at 24. FIG. 3 is an exploded view and FIG. 4 is a cross sectional view. The presently preferred sensor is based on the technology described in the Colvin patents but has a chemistry adapted to detection of nitric oxide. A circuit board 40 has a plurality of pins 42 extending downwardly for interconnecting the sensor with other components. An LED 44 is mounted generally to the center of the top of the circuit board. A pair of photodiodes 46 and 48 are also mounted to the top of the circuit board. The photodiodes are mounted symmetrically on opposite sides of, and a short distance from, the LED 44. An optical filter is mounted on top of each photodiode; filter 50 is mounted on photodiode 46 and filter 52 is mounted on photodiode 48. The optical filters preferably are bonded to the photodiodes with an optically clear adhesive.

A heat spreader 54, preferably a thin copper sheet with down-turned edges, is mounted to the top of the circuit board. The heat spreader has a downwardly extending foot 56 at each of its four corners, each of which engage a hole 58 in the circuit board 40. The feet and the down-turned edges of the heat spreader 54 support the central portion of the heat spreader a short distance above the circuit board, leaving a gap therebetween. The LED 44, the photodiodes 46 and 48, and the filters 50 and 52 are disposed in this gap between the circuit board and the heat spreader. Two round holes 60 are cut in the heat spreader, one hole being directly above each of the photodiodes 46 and 48. Two pieces of glass substrate 62 and 64 are mounted to the top of the heat spreader, with one piece being mounted directly on top of each of the holes 60. As shown, these pieces of substrate 62 and 64 are square. A circle of fluorescent film is formed on top of each of the pieces of substrate; film circle 66 is formed on substrate 62 and film circle 68 is formed on substrate 64. A gas impermeable glass cover 70 is disposed over film circle 66 and bonded to the glass substrate 62 with epoxy 72. Therefore, film circle 66 is sealed in by the cover 70 above and the epoxy 72 at the edges. This results in one of the film circles, 68, being exposed to the surrounding atmosphere, while the other film circle, 66, is sealed in and not exposed. Therefore, film circle 66 does not react to changes in nitric oxide concentration while film circle 68 does. Film circle 68 will be referred to as a sensing region and film circle 66 will be referred to as a reference region. The substrates 62 and 64 and the materials applied to them form the sensing face of the sensor.

Referring again to FIG. 4, the gap between the circuit board 40 and the heat spreader 54, as well as the holes 60, are filled with an optically clear waveguide material 74. The waveguide material 74 serves to optically couple the LED 44 to the glass substrates 62 and 64, making the substrates an integral part of the waveguide. The waveguide material also optically couples the sensing region 68 and reference region 66 to the filters 50 and 52 and the photodiodes 46 and 48. The result is a continuous optical waveguide that optically couples these components. Suitable waveguide materials are manufactured by Norland Products of New Brunswick, N.J., and by Epoxy Technology of Bilerica, Mass., the latter under the name EPOTEK®.

In order to avoid problems with condensation forming on the sensing region 68 and the reference region 66, the regions are preferably both warmed using the heat spreader 54. For this purpose, small heaters 76, comprising resistors, are mounted to the circuit board 40 adjacent each of the foot mounting holes 58. The heat spreader feet 56 are soldered into the holes, and to the heaters 76 so that heat is transferred into the spreader. A thermistor 78 is mounted to the circuit board 40 in a position such that it contacts one of the down-turned edges of the heat spreader 54 when the sensor is assembled. The thermistor may be soldered to the edge to improve heat transfer. The thermistor is then used to monitor the temperature of the heat spreader, and the heaters are controlled so as to maintain a generally constant temperature. An EEPROM, containing calibration data for the sensor, may be mounted to the underside of the circuit board.

The fluorescent films 66 and 68 are formed of materials whose fluorescence or absorbance characteristics change as a function of nitric oxide concentration. As an example, thiol or sulfhydryl may be joined to a fluorophore such as pyrene giving sulfhydrylpyrene). In this respect, an article entitled "Determination of Nitric Oxide Levels by Fluorescence Spectroscopy" by G. Gabor and N. Allon, published in the *Biochemical, Pharmacological, and Clinical Aspects of Nitric Oxide* (Edited by B. A. Weissman et al., Plenum Press, New York, 1995) is incorporated herein in its entirety.

Radiation from the LED is transmitted to the sensing region 68 and the reference region 66 by the optical waveguide material 74. The wavelength emission of the LED 44 is chosen to induce fluorescence from the fluorescent film regions 66 and 68. Fluorescence emissions from the sensing and reference regions, preferably shifted in wavelength compared to the LED radiation, are detected by the two photodiodes. Photodiode 46 detects fluorescence from the reference region 66, and photodiode 48 detects fluorescence from the sensing region 68. The optical filters 50 and 52 overlie the photodiodes, to pass the fluorescence radiation while rejecting other wavelengths, in particular the excitation radiation from the LED. The optical filters 50 and 52 may be an epoxy coating, a glass filter, or a polymeric-based sheet material. Preferably, a prefabricated polymeric-based sheet material is used. The emissions from the LED 44 and the fluorescence emissions from the films 66 and 68 pass through holes 60 in the plate 54. Preferably, the film circles 66 and 68, the holes 60, and the active areas of the photodiodes 46 and 48 are all circles of similar diameter.

During nitric oxide sensing measurements, the substrates 62 and 64 and sensing region 68 and reference region 66 preferably are maintained at a temperature sufficient to reduce problems associated with moisture condensation. The heating of the substrate is achieved by passing electrical current through the four surface-mounted resistors 76. The temperature of the copper plate 54 is monitored by the thermistor 78, allowing the heating current through the resistors and temperature to be regulated. If moisture was eliminated from the gas flow by some means, e.g. chemical drying, water absorbing/adsorbing substances, membranes, filters, foam sheets, etc., or prevented from condensing on the fluorescent film, such as by some surface treatment (a nitric oxide-permeable hydrophobic film or other approaches), then the sensor need not be heated.

The thin fluorescent films used in the nitric oxide sensor respond very rapidly to changes in nitric oxide concentration thereby providing the sensor with instantaneous response, as that term is defined herein. The sensor has a response time preferably less than or equal to 200 milliseconds, and most preferably less than or equal to 100 ms. Even faster response times may be preferable for certain applications.

Additional details concerning the present approach to component gas concentration sensing may be obtained by reference to the discussion of a similar oxygen sensor in Applicant's co-pending patent application Ser. No. 09/630, 398, incorporated herein in its entirety by reference. As will be clear to those of skill in the art, other types of nitric oxide concentration sensors may be used as long as they have an instantaneous response and are not sampling-based sensors. Also, the concentration of other component gases may be monitored using a meter similar to the one illustrated in the present invention. For example, an oxygen sensor may be added or may be substituted for the nitric oxide sensor so as to construct a calorimeter is accordance with Applicant's co-pending patent application Ser. No. 09/630,398.

In the simplest embodiment of the present invention, the nitric oxide concentration sensor is provided on the side of the flow tube, and flow sensors are not provided. In this embodiment, instantaneous nitric oxide concentrations may be monitored during respiration providing a curve of nitric oxide concentrations. This data may be useful in the diagnosis and treatment of various diseases without obtaining flow data. In a more complicated, and preferred, embodiment of the present invention, flow sensors as previously discussed are also included. The flow sensors allow for determination of many additional parameters, including many respiratory parameters such as flow rate, flow volume, lung capacity, and others. For example, by including flow sensors, the meter can be used as a spirometer. The peak flow, the forced vital capacity (FVC), and the forced expiratory volume during the first second (FEV 1) may be derived from the collected data. The nitric oxide data, such as the time dependent concentration, may be combined with these parameters. A modified version of the present invention may also be used to determine functional residual capacity as explained in U.S. Pat. Nos. 5,540,233 to Larsson et al and 5,957,128 to Hecker et al, both of which are incorporated herein by reference.

Figure 5:
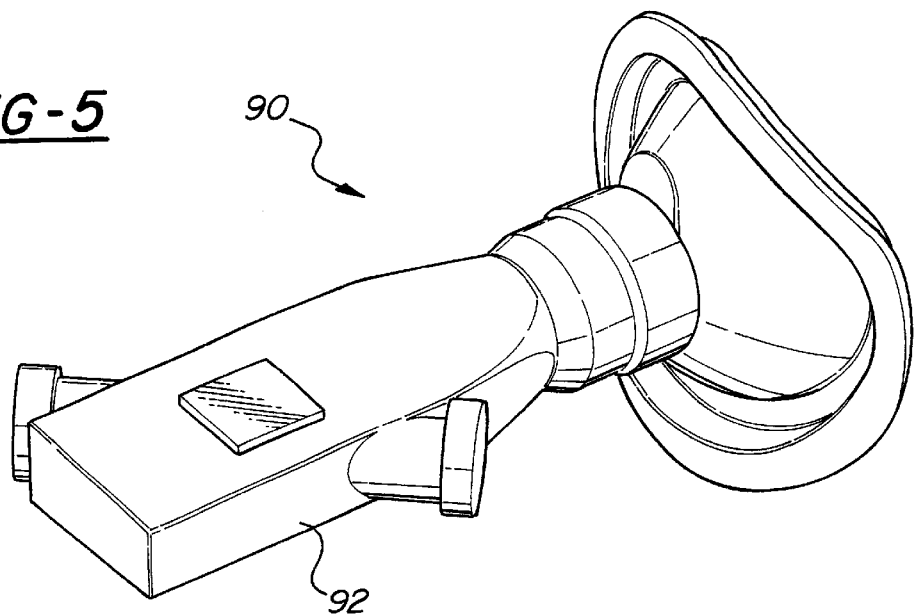
FIG. 5 is a perspective view of a first alternative embodiment of a respiratory nitric oxide meter according to the present invention.

Referring now to FIG. 5, a first alternative embodiment of a nitric oxide meter according to the present invention is generally shown at 90. This embodiment of the present invention differs from the previous embodiment in that the flow pathway or flow tube 92 is generally rectangular in cross-section. This illustrates that the flow tube does not necessarily have to be circular in cross-section.

Figure 6:
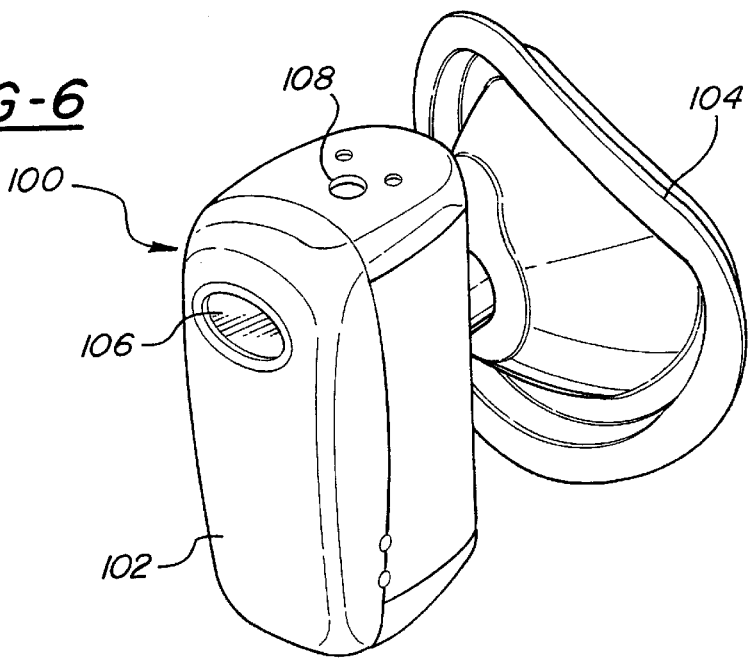
FIG. 6 is a perspective view of a second alternative embodiment of a nitric oxide meter according to the present invention.
Figure 7:
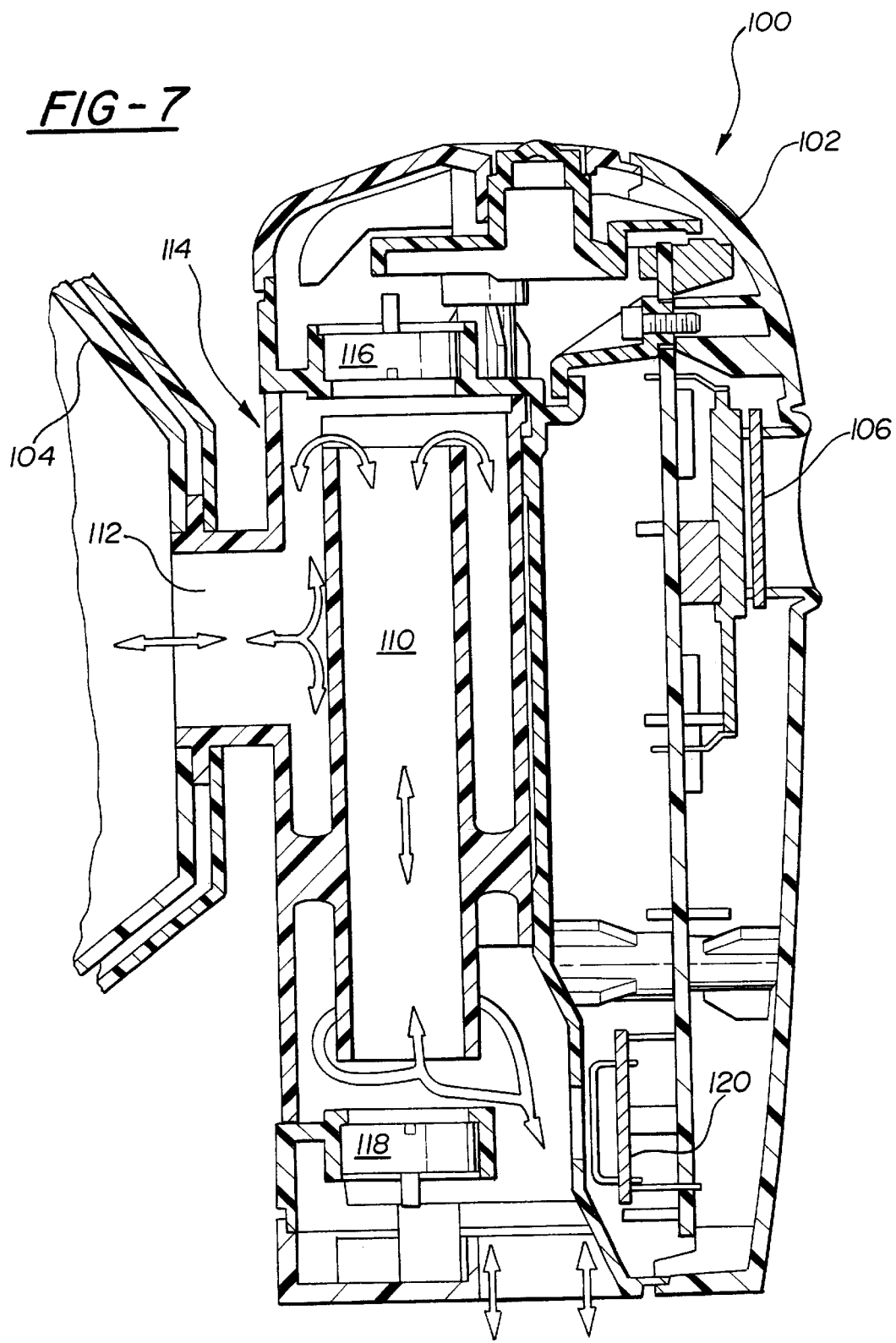
FIG. 7 is a cross-sectional view of the meter of FIG. 6 taken along lines 7—7.

Referring now to FIGS. 6 and 7, a second alternative embodiment of a nitric oxide meter according to the present invention is generally shown at 100. This embodiment has a configuration similar to the configuration of the calorimeter described in Applicant's co-pending patent application Ser. No. 09/630,398. Details of this embodiment may be obtained by referenced to the co-pending application. Basically, the meter 100 includes a body 102 with a mask 104 extending therefrom. A display 106 is arranged on one side of the body 102 and a combination control button and indicator light 108 is disposed on another side of the body 102. Referring to FIG. 7, a cross-section of this embodiment is illustrated. Unlike with the previous embodiment, the flow pathway is not a straight through design. Instead, the respiration gases follow a path generally indicated by arrows A through G through the body 102 and mask 104 of the meter 100. The flow tube 110 is arranged perpendicularly to the flow of respiration gases to and from the mask 104. An inlet conduit 112 interconnects the mask 104 with the flow tube housing 114. Ultrasonic flow sensors 116 and 118 are arranged above and below the ends of the flow tube 110 so as to measure the flow coaxially. Unlike the embodiment of FIGS. 1 and 2, calculation of flow velocity does not require correction for the flow sensors being arranged at an angle to the flow. This embodiment also differs from the previous embodiments in that the nitric oxide sensor 120 is positioned adjacent the flow pathway but below the bottom end of the flow tube 110. A nitric oxide meter according to the present invention may also be constructed in accordance with the other embodiments of the calorimeter discussed in Applicant's co-pending application Ser. No. 09/630,398, by substituting a nitric oxide sensor, as previously described, for the oxygen sensor used with a calorimeter. Other calorimeter designs that may be modified according to the present invention are disclosed in U.S. Pat. Nos. 4,917,108; 5,038, 792; 5,178,155; 5,179,958; and 5,836,300, all to Mault, a co-inventor of the present application, are incorporated herein by reference.

As will be clear to those of skill in the art, it may be beneficial to provide a nitric oxide meter which may be sanitarily used by multiple users without significant risk of transfer of germs. Referring again to FIG. 2, the mask 14 may include a biological filter 15 disposed therein to prevent the transfer of biological materials into the body 12 of the meter 10 from the mask 14. One example of a biological filter material 15 is Filtrete® from 3M. The use of the biological filter material allows the mask 14 and/or the filter material 15 to be changed between users so as to provide sanitation. Other approaches to providing sanitary respiratory devices are described in Applicant's copending patent application Ser. No. 09/630,398.

Figure 8:
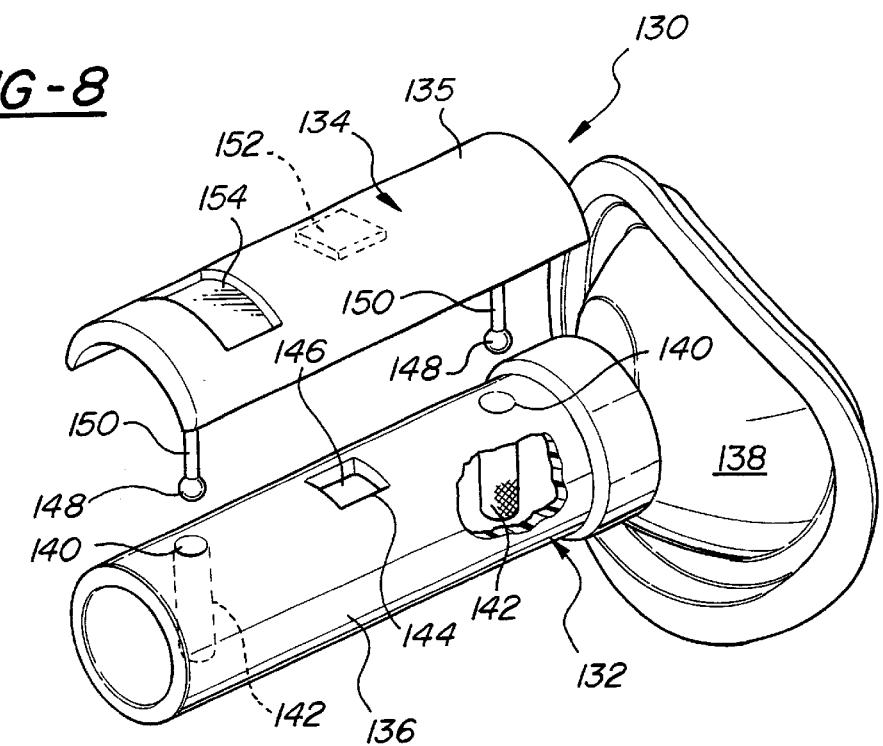
FIG. 8 is a perspective view, partially exploded, of a third alternative embodiment of the nitric oxide meter according to the present invention.

Referring now to FIG. 8, a third alternative embodiment of a nitric oxide meter according to the present invention is generally shown at 130. This embodiment is also designed for use by multiple users while providing sanitation. It includes a disposable portion 132 and a reusable portion 134. The disposable portion includes a flow tube 136, which is generally cylindrical and of constant cross-section, extending perpendicularly from a respiratory connector such as a mask 138. A pair of openings 140 are disposed in the upper side of the flow tube 136 near opposite ends of the flow tube. Extending downwardly within the flow tube from the openings 140 are ultrasonically transparent, sanitary barrier socks 142. Alternatively, the socks could be replaced with more rigid structures with ultrasonically transparent windows therein. A third opening 144 is disposed in the upper side of the flow tube and has a piece of sanitary barrier material 146 disposed therein.

The reusable portion 134, is configured to mate with the upper side of the flow tube 136. The reusable portion has an elongated arcuate body 135 with a pair of ultrasonic transducers 148 extending downwardly from the body 135 on posts 150. The ultrasonic transducers 148 and posts 150 are sized and positioned so as to enter the openings 140 in the disposable portion 132 when the reusable portion 134 is mated therewith. When the two portions are coupled, the ultrasonic transducers 148 are positioned approximately in the center of the flow tube 136 within the sanitary barrier socks 142. The ultrasonic transducers 148 are preferably of the small, micromachined type and work as previously described. However, because they are positioned within the flow tube itself, the pulses traveling between the ultrasonic sensors are coaxial with the flow and do not require correction based on ultrasonic pulses traveling at an angle to the flow. A nitric oxide sensor, as previously described, is also supported on the body 135 of the reusable portion 134, and is generally indicated at 152. It is sized and positioned so as to fit into the third opening 144 in the upper side of the flow tube so that it is in contact with the flow within the flow tube, but protected from biological contamination by the filter material 146. A display 154 may also be provided on the reusable portion 134. In this embodiment, the reusable portion 134 may be retained for multiple uses and users while the disposable portion is specific to an individual user. As explained in Applicant's co-pending patent application Ser. No. 09/630,398, the meter of FIGS. 6 and 7 may also include a disposable and a reusable portion.

Figure 9:
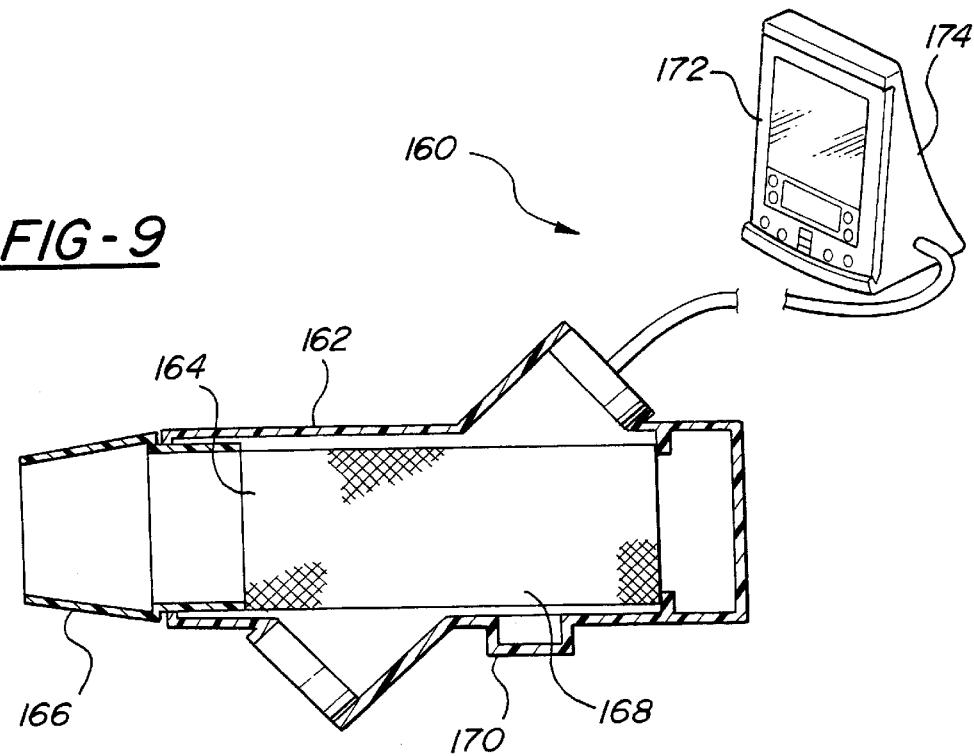
FIG. 9 is a view of a nitric oxide metering system according to the present invention with the meter portion shown in cross-section.

Referring now to FIG. 9, another embodiment of a nitric oxide meter according to the present invention is generally shown at 160. This embodiment is similar to the first embodiment of the present invention in that the meter 160 includes a generally cylindrical flow tube 162 with the ultrasonic flow sensors being disposed in side passages angled to the flow tube. However, in this embodiment, a disposable insert 164 which includes a mouthpiece 166 and a sanitary sleeve 168. The sleeve portion 168 of the insert 164 slides into the flow tube 162 so as to line the flow tube. The sleeve is ultrasonically transparent so that the ultrasonic flow sensors can monitor flow through the sleeve 168. A nitric oxide sensor 170 is disposed in the underside of the flow tube 162 so as to be in contact with flow through the sleeve 168. The sleeve is either porous to nitric oxide or includes a window having material that. allows the passage of nitric oxide. As a further aspect of the present invention, data processing, storage, and analysis may be performed by a remote computing device such as a personal digital assistant (PDA) 172. The PDA 172 is docked into an interface 174 which is wired to the sensor body. Alternatively, data may be transferred between the sensor and the PDA by wireless means or by transfer of memory modules which store data, as described in Applicant's co-pending patent application Ser. No. 09/669,125, incorporated herein in its entirety by reference. Also, the nitric oxide meter may communicate with other remote devices, such as stationary or portable computers and remote devices such as servers via the Internet or dock or interconnect with a PDA, as also described in the co-pending application. These alternatives apply to all embodiments of the present invention.

Figure 10:
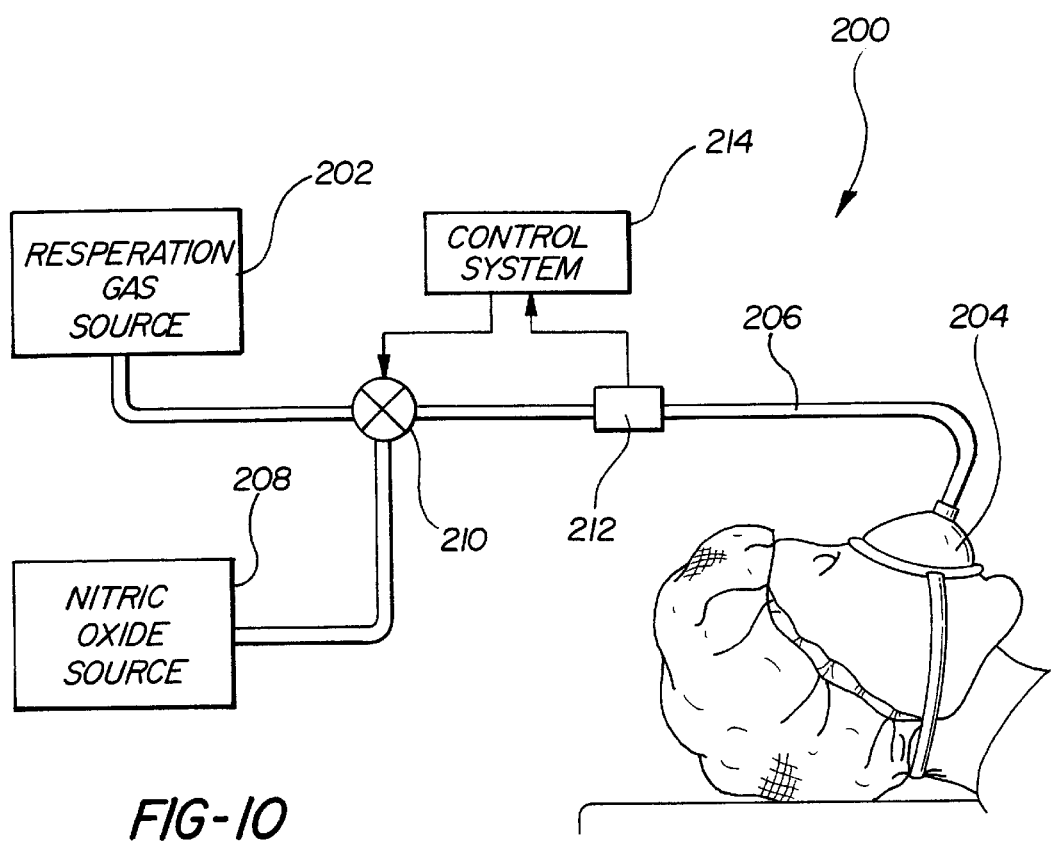
FIG. 10 is a schematic of a nitric oxide administration system utilizing a nitric oxide meter according to the present invention.

Referring now to FIG. 10, an additional aspect of the present invention will be discussed. As explained in the Background, administration of nitric oxide to the respiratory system of a patient is beneficial in the treatment of some disorders. A system for the controlled administration of nitric oxide to a patient is generally shown at 200 in FIG. 10. The system includes a respiration gas source 202 which is interconnected with respiratory connector 204 by a conduit 206. The respiratory connector may be of any type, such as a mask or a connector for intubating the patient. A nitric oxide source 208 is also provided and is interconnected with the conduit 206 by a control valve 210. A nitric oxide meter 212 according to the present invention is disposed in the conduit 206 so that respiration gases mixed with nitric oxide flowing through the conduit 206 pass through the meter 212. A control system 214 is interconnected with the meter 212 and the control valve 210 so as to provide feedback control of the nitric oxide administration system. Meter 212 may be constructed according to any of the embodiments of the present invention and includes a nitric oxide sensor operable to determine the instantaneous concentration of nitric oxide in the respiration gases flowing through the meter. The output of the meter 212 is fed to the control system 214. The control system 214 then controls the control valve 210 so as to maintain the desired concentration of nitric oxide flowing through the conduit 206. As will be clear to those of skill in the art, the system 200 may be used with any of the approaches of administering controlled amounts of nitric oxide as described in the prior art. For example, pulses of nitric oxide may be administered to the patient rather than having continuous flow. The meter 212 is useful in determining the changing quantity of nitric oxide during such an administration procedure. As will be clear to those of skill in the art, the system 200 may also be configured as a forced respiration system for patients requiring assistance in respiration or as part of an anesthesia system. Alternatively, the nitric oxide meter 212 may monitor both inhalation and exhalation. In this case the meter is preferably very close to the connector 204 to minimize dead air space. Instead, two meters may be used.

As will be clear to those of skill in the art, various alterations may be made to the above-described embodiments of the present invention without departing from its scope or teaching. For example, the nitric oxide meters could include graphic displays to show profiles of nitric oxide, breath flow, or other parameters for a period of time such as a single breath or one minute. Data may also be averaged over multiple breaths to provide an averaged profile. The meter, or other devices used with the meter, may include a memory and a processor to store flow profiles or nitric oxide profiles indicative of various physiological conditions including a healthy normal state and various physiological disorders. The meter or associated computational device may then compare the patient's data with the stored profiles in order to make a preliminary diagnosis. A PDA may interconnect with the nitric oxide meter and provide the necessary display and processing as well as diagnosis. Other alternatives will also be clear to those of skill in the art. It is the following claims, including all equivalents, which define the scope of the present invention.

I claim:

1. A respiratory nitric oxide meter for measuring the nitric oxide content of respiration gases for a subject, said meter comprising:

a respiratory connector configured to be disposed in fluid communication with the respiratory system of the subject so as to pass inhalation and exhalation respiratory gases as the subject breathes;

a flow pathway operable to receive and pass the respiration gases, said flow pathway having a first end in fluid communication with the respiratory connector and a second end in fluid communication with a reservoir of respiratory gases;

a nitric oxide concentration sensor operable to generate electrical signals as a function of the instantaneous fraction of nitric oxide in the respiration gases as the gases pass through said flow pathway;

and a one-way valve located between said respiratory connector and said first end of the flow pathway;

said one-way valve being presettable in a first position effective to pass inhalation gases directly into the respiratory connector bypassing said flow pathway, and to pass exhalation gases through said flow pathway so as to contact said nitric oxide concentration sensor, to thereby sense the nitric oxide concentration in the exhalation gases;

said one-way valve being presettable in a second position effective to pass exhalation gases directly from the respiratory connector bypassing said flow pathway, and to pass inhalation gases through said flow pathway so as to contact said nitric oxide concentration sensor, to thereby sense the nitric oxide concentration in the inhalation gases.

2. The respiratory nitric oxide meter according to claim 1, wherein said second end of the flow pathway is connected to the atmosphere, constituting said reservoir of respiratory gases.

3. The respiratory nitric oxide meter according to claim 1, wherein said second end of the flow pathway is connected to a source of respiratory gases, constituting said reservoir of respiratory gases.

4. The respiratory nitric oxide meter according to claim 1, wherein said nitric oxide concentration sensor has a response time of less than 200 ms to enable instantaneous analysis during a single breath.

5. The respiratory nitric oxide meter according to claim 1, wherein said flow pathway comprises a generally cylindrical flow tube and said nitric oxide sensor is supported on said tube.

6. The respiratory nitric oxide meter according to claim 5, wherein said flow tube has a side wall with an opening defined therein and said nitric oxide sensor is at least partially disposed in said opening.

7. The respiratory nitric oxide meter according to claim 6, wherein said nitric oxide sensor is carried on a unit which is attachable to and detachable from said flow tube such that said unit carrying the nitric oxide sensor is reusable with different flow tubes and respiratory connectors.

8. A respiratory nitric oxide meter for measuring a nitric oxide content of respiration gases for a subject, the subject having a respiratory system, said meter comprising:

a respiratory connector configured to be disposed in fluid communication with the respiratory system of the subject so as to pass respiration gases as the subject breathes;

a flow pathway operable to receive and pass respiration gases, the flow pathway having a first end in fluid communication with the respiratory connector and a second end in fluid communication with a reservoir of respiratory gases;

a flow meter configured to generate a first electrical signal as a function of an instantaneous flow of respiration gases passing through said flow pathway;

a nitric oxide concentration sensor operable to generate a second electrical signal as a function of an instantaneous fraction of nitric oxide in the respiration gases as the respiration gases pass through said flow pathway; and a one-way valve located between said respiratory connector and said first end of the flow pathway;

said one-way valve being presettable in a first position effective to pass inhalation gases directly into the respiratory connector bypassing said flow pathway, and to pass exhalation gases through said flow pathway so as to contact said nitric oxide concentration sensor, to thereby sense a nitric oxide concentration in the exhalation gases;

said one-way valve being presettable in a second position effective to pass exhalation gases directly from the respiratory connector bypassing said flow pathway, and to pass inhalation gases through said flow pathway so as to contact said nitric oxide concentration sensor, to thereby sense a nitric oxide concentration in the inhalation gases.

* * * * *